(12) United States Patent
Ahmadpour

(10) Patent No.: US 10,450,535 B2
(45) Date of Patent: Oct. 22, 2019

(54) SHELF-STABLE HYDROGEN PEROXIDE ANTIMICROBIAL COMPOSITIONS

(71) Applicant: VIROX TECHNOLOGIES INC., Oakville, Ontario (CA)

(72) Inventor: Faraz Ahmadpour, Mississauga (CA)

(73) Assignee: VIROX TECHNOLOGIES INC., Oakville, Ontario (CA)

(*) Notice: Subject to any disclaimer, the term of this patent is extended or adjusted under 35 U.S.C. 154(b) by 118 days.

(21) Appl. No.: 15/786,632

(22) Filed: Oct. 18, 2017

(65) Prior Publication Data

US 2019/0112553 A1  Apr. 18, 2019

(51) Int. Cl.
C11D 3/43 (2006.01)
C11D 3/39 (2006.01)
(Continued)

(52) U.S. Cl.
CPC ............ *C11D 3/3942* (2013.01); *A01N 37/10* (2013.01); *A01N 37/40* (2013.01); *A01N 41/04* (2013.01);
(Continued)

(58) Field of Classification Search
CPC ................ C11D 3/48; C11D 3/3942
(Continued)

(56) References Cited

U.S. PATENT DOCUMENTS 2,528,378 A   10/1950 Mannheimer
3,969,258 A    7/1976 Carandang et al.
(Continued)

FOREIGN PATENT DOCUMENTS

CA   1 102 502   6/1981
CA   1 244 759   11/1988
(Continued)

OTHER PUBLICATIONS

Baldry, M..G.C., "The bactericidal, fungicidal and sporicidal properties of hydrogen perioxide and peracetic acid", Journal of Applied Bacteriology, 34, 417-423, and especially p. 418 (top left column) and 421 (top right column) thereof, 1982.
(Continued)

*Primary Examiner* — Gregory E Webb
(74) *Attorney, Agent, or Firm* — Clark & Brody

(57) ABSTRACT

A disinfecting solution includes hydrogen peroxide at a concentration of from about 1.5% w/w to 8% w/w; at least one readily biodegradable anionic surfactant in a concentration of from about 10% w/w to about 25% w/w; at least one of salicylic acid and salts thereof, in a concentration of from about 1% w/w to about 8% w/w; at least one chelating agent in a concentration of from about 0.005% w/w to about 10% w/w; and at least one low-corrosive non-surfactant sulfonic acid selected from benzenesulfonic acid, benzene disulfonic acid, xylene sulfonic acid, toluene sulfonic acid, cumene sulfonic acid, sulfosalicylic acid, naphthalene mono- or di-sulfonic acid, methane sulfonic acid, and isethionic acid in a concentration of from about 1% w/w to about 15% w/w. The solution is free of acetic acid, furoic acid, phenylacetic acid, cationic surfactants, amphoteric surfactants, aromatic alcohols, halogen acids, phenols, peracid activators, bleaches, and (optionally) benzoic acid.

24 Claims, 2 Drawing Sheets

(51) Int. Cl.
| | | |
|---|---|---|
| *C11D 1/22* | (2006.01) | |
| *C11D 1/83* | (2006.01) | |
| *C11D 3/20* | (2006.01) | |
| *A01N 41/04* | (2006.01) | |
| *C11D 3/34* | (2006.01) | |
| *A01N 59/00* | (2006.01) | |
| *A01N 37/10* | (2006.01) | |
| *A01N 37/40* | (2006.01) | |
| *C11D 3/48* | (2006.01) | |
| *C11D 1/12* | (2006.01) | |
| *C11D 1/14* | (2006.01) | |
| *C11D 3/33* | (2006.01) | |
| *C11D 3/36* | (2006.01) | |
| *C11D 1/72* | (2006.01) | |

(52) U.S. Cl.
CPC ............ *A01N 59/00* (2013.01); *C11D 1/123* (2013.01); *C11D 1/143* (2013.01); *C11D 1/146* (2013.01); *C11D 1/22* (2013.01); *C11D 1/83* (2013.01); *C11D 3/2086* (2013.01); *C11D 3/33* (2013.01); *C11D 3/34* (2013.01); *C11D 3/3409* (2013.01); *C11D 3/3418* (2013.01); *C11D 3/3472* (2013.01); *C11D 3/361* (2013.01); *C11D 3/3947* (2013.01); *C11D 3/43* (2013.01); *C11D 3/48* (2013.01); *C11D 1/72* (2013.01)

(58) Field of Classification Search
USPC ........................................ 510/302, 309, 375
See application file for complete search history.

(56) References Cited

U.S. PATENT DOCUMENTS

| | | | |
|---|---|---|---|
| 4,051,058 A | 9/1977 | Bowing | |
| 4,051,059 A | 9/1977 | Bowing et al. | |
| 4,405,482 A | 9/1983 | Hayes et al. | |
| 4,446,153 A | 5/1984 | Yang | |
| 4,477,438 A | 10/1984 | Willcockson et al. | |
| 4,518,585 A | 5/1985 | Greene et al. | |
| 4,525,291 A | 6/1985 | Smith et al. | |
| 4,525,292 A | 6/1985 | Cushman et al. | |
| 4,557,898 A | 12/1985 | Greene et al. | |
| 4,637,899 A | 1/1987 | Kennedy, Jr. | |
| 4,717,737 A | 1/1988 | Kern | |
| 4,878,951 A | 11/1989 | Pochard et al. | |
| 5,059,417 A | 10/1991 | Williams et al. | |
| 5,149,463 A | 9/1992 | Peterson | |
| 5,171,564 A | 12/1992 | Nathoo et al. | |
| 5,200,189 A | 4/1993 | Oakes et al. | |
| 5,205,960 A | 4/1993 | Kristopeit et al. | |
| 5,244,593 A | 9/1993 | Roselle et al. | |
| 5,264,229 A | 11/1993 | Mannig et al. | |
| 5,376,387 A | 12/1994 | Monticello | |
| 5,387,605 A | 2/1995 | Beilfuss et al. | |
| 5,523,012 A | 6/1996 | Winterton et al. | |
| 5,599,400 A | 2/1997 | Mao et al. | |
| 5,602,090 A | 2/1997 | Melikyan et al. | |
| 5,641,530 A | 6/1997 | Chen | |
| 5,718,910 A | 2/1998 | Oakes et al. | |
| 5,723,400 A | 3/1998 | Morini et al. | |
| 5,723,406 A | 3/1998 | Larose et al. | |
| 5,728,666 A | 3/1998 | Vitomir | |
| 5,736,498 A | 4/1998 | Gray | |
| 5,736,582 A | 4/1998 | Devillez | |
| 5,827,542 A | 10/1998 | Miner et al. | |
| 5,855,217 A | 1/1999 | John | |
| 5,891,392 A | 4/1999 | Monticello et al. | |
| 5,900,256 A | 5/1999 | Scoville, Jr. et al. | |
| 6,043,209 A | 3/2000 | Micciche et al. | |
| 6,096,348 A | 8/2000 | Miner et al. | |
| 6,110,883 A | 8/2000 | Petri et al. | |
| 6,165,957 A | 12/2000 | Vitomir | |
| 6,296,880 B1 | 10/2001 | Murad | |
| 6,309,470 B1 | 10/2001 | Schulhoff et al. | |
| 6,346,279 B1 | 2/2002 | Rochon | |
| 6,383,523 B1 | 5/2002 | Murad | |
| 6,444,636 B1 | 9/2002 | Toussaint et al. | |
| 6,465,405 B1 | 10/2002 | Vitomir | |
| 6,479,454 B1 | 11/2002 | Smith et al. | |
| 6,555,509 B2 | 4/2003 | Abbas et al. | |
| 6,593,283 B2 | 7/2003 | Hei et al. | |
| 6,617,294 B2 | 9/2003 | Narula et al. | |
| 6,627,589 B1 | 9/2003 | Arvanitidou | |
| 6,686,324 B2 | 2/2004 | Ramirez et al. | |
| 6,803,057 B2 | 10/2004 | Ramirez et al. | |
| 6,841,090 B1 | 1/2005 | Allighieri et al. | |
| 6,927,237 B2 | 8/2005 | Hei et al. | |
| 7,354,604 B2 | 4/2008 | Ramirez et al. | |
| 7,632,523 B2 | 12/2009 | Ramirez et al. | |
| 8,637,085 B2 | 1/2014 | Ramirez et al. | |
| 8,808,755 B2 | 8/2014 | Omidbakhsh | |
| 8,865,196 B2 | 10/2014 | Omidbakhsh | |
| 8,999,400 B2 | 4/2015 | Ramirez et al. | |
| 9,198,935 B2 | 12/2015 | Omidbakhsh et al. | |
| 9,233,180 B2 | 1/2016 | Omidbakhsh et al. | |
| 9,271,494 B2 | 3/2016 | Pedersen et al. | |
| 2002/0072288 A1 | 6/2002 | Hei et al. | |
| 2002/0142051 A1 | 10/2002 | Rochon | |
| 2002/0155969 A1 | 10/2002 | Rees et al. | |
| 2002/0168422 A1 | 11/2002 | Hei et al. | |
| 2002/0192297 A1 | 12/2002 | Ramirez et al. | |
| 2003/0078178 A1 | 4/2003 | Ramirez et al. | |
| 2003/0161891 A1 | 8/2003 | Ruiter | |
| 2003/0180377 A1 | 9/2003 | Ramirez et al. | |
| 2003/0181377 A1 | 9/2003 | Hallahan et al. | |
| 2003/0203035 A1 | 10/2003 | Hasan et al. | |
| 2003/0206965 A1 | 11/2003 | Hasan et al. | |
| 2003/0228996 A1 | 12/2003 | Hei et al. | |
| 2004/0033923 A1 | 2/2004 | McClung | |
| 2004/0137077 A1 | 7/2004 | Ancira et al. | |
| 2004/0171687 A1 | 9/2004 | Kemp et al. | |
| 2004/0182793 A1 | 9/2004 | Owens | |
| 2005/0019421 A1 | 1/2005 | Hobbs et al. | |
| 2005/0058719 A1 | 3/2005 | Ramirez et al. | |
| 2005/0133460 A1 | 6/2005 | McClung | |
| 2005/0145824 A1 | 7/2005 | McClung | |
| 2005/0145825 A1 | 7/2005 | McClung | |
| 2005/0145826 A1 | 7/2005 | McClung | |
| 2005/0255172 A1 | 11/2005 | Omidbakhsh | |
| 2006/0035808 A1* | 2/2006 | Ahmed .................. C11D 1/40 510/499 |
| 2006/0172911 A1 | 8/2006 | McClung | |
| 2006/0199206 A1 | 9/2006 | Wang et al. | |
| 2006/0285995 A1 | 12/2006 | Hobbs et al. | |
| 2007/0059380 A1 | 3/2007 | Ramirez et al. | |
| 2011/0262557 A1* | 10/2011 | Omidbakhsh .......... A01N 37/10 424/616 |
| 2014/0044596 A1* | 2/2014 | Ramirez ................ A01N 59/00 422/28 |
| 2018/0187129 A1* | 7/2018 | Traistaru .............. C11D 1/825 |

FOREIGN PATENT DOCUMENTS

| | | |
|---|---|---|
| CA | 2 475 327 | 8/2003 |
| CA | 2 503 627 | 6/2004 |
| CA | 2454437 | 6/2005 |
| CA | 2564763 | 11/2005 |
| CA | 2733644 | 4/2010 |
| CA | 2786573 | 7/2011 |
| DE | 32 29 097 | 2/1984 |
| DE | 35 43 500 | 6/1987 |
| EP | 0 057 153 | 8/1982 |
| EP | 0 087 049 | 8/1983 |
| EP | 0 127 557 | 12/1984 |
| EP | 0 252 278 | 1/1988 |
| EP | 0 289 463 | 11/1988 |
| EP | 0 351 772 | 1/1990 |
| EP | 0 456 272 | 11/1991 |
| EP | 0 505 935 | 9/1992 |
| EP | 0 517 996 | 12/1992 |
| EP | 0 524 150 | 1/1993 |
| EP | 0 582 359 | 2/1994 |

(56) References Cited

FOREIGN PATENT DOCUMENTS

| | | |
|---|---|---|
| EP | 0 582 360 | 2/1994 |
| EP | 0 776 613 | 6/1997 |
| EP | 0 845 526 | 6/1998 |
| EP | 1 118 656 | 7/2001 |
| EP | 1 369 037 | 12/2003 |
| EP | 1 374 679 | 1/2004 |
| EP | 1 388 575 | 2/2004 |
| EP | 1 955 593 | 8/2008 |
| GB | 1 584 170 | 2/1981 |
| GB | 2 101 350 | 1/1983 |
| JP | 10-130693 | 5/1998 |
| WO | 93-04664 | 3/1993 |
| WO | 93/14183 | 7/1993 |
| WO | 95/04001 | 2/1995 |
| WO | 96/20737 | 7/1996 |
| WO | 97/28691 | 8/1997 |
| WO | 98/11777 | 3/1998 |
| WO | 98/18894 | 5/1998 |
| WO | 98/21305 | 5/1998 |
| WO | 98/59028 | 12/1998 |
| WO | 99/02638 | 1/1999 |
| WO | 99/03446 | 1/1999 |
| WO | 99/19441 | 4/1999 |
| WO | 99/27066 | 6/1999 |
| WO | 99/52360 | 10/1999 |
| WO | 00/27981 | 5/2000 |
| WO | 02/055647 | 7/2002 |
| WO | 03/005817 | 1/2003 |
| WO | 03/005818 | 1/2003 |
| WO | 03/067989 | 8/2003 |
| WO | 03/076560 | 9/2003 |
| WO | 2004/035718 | 4/2004 |
| WO | 2004/045281 | 6/2004 |

OTHER PUBLICATIONS

Sattar S.A., Springthrope, S. and M. Rochon, "A product based on accelerated and stabilized hydrogen peroxide, evidence for broad-spectrum germicidal activity", Can. J. Infection Control, Winter 1998, vol. 13, No. 4.

Lopes, J.A., "Evaluation of dairy and food plant sanitizers against *Salmonella typhimurium* and listeria momocytogenes", J. Dairy Sci., 1969, 2791-2796.

Disinfection, Sterilization and Preservation, $4^{th}$ ed. Seymour S. Block, Lea & Febinger 1991 pp. 167-172, 178-180, 256-261, 263-271.

Bio-Soft S-101, Stepan (2012) download from http://www.stepan.com/templates/product.aspx?id=2375, Oct. 10, 2013.

Parker & Litchfield, "Food Plant Sanitation", 1962, pp. 223-263.

Database Chemabs 'Online! Chemical Abstracts Service, Columbus, OH, US; XP002287350; retrieved from STN—International Database accession No. 136:351642—abstract (2002).

XP-002287351: "Biol Instr Mfr Res Inst"; Database WPI published by Derwent Publications Ltd.; abstract only; c. Jul. 27, 1996.

XP-002287352: "(Wang-I) Wang L"; Database WPI published by Derwent Publications Ltd.; abstract only; 1999.

XP-002287349: "Surface-Active Agents: Acid-Anionic Compounds" by G. R. Dychdala et al.; *Disinfection, Sterilization and Preservation*; c. 1991.

"Announcement", 1999, The Canadian Journal of Infection Control; vol. 14, No. 1.

Dowfax Hydrotope Solution: "Alkyldiphenyloxide Disulfonate Salts", Copyright The Dow Chemical Company (1995-2006): http://www.dow.com/furfactants/products/alkyl_sa.htm.

Dow, Product Safety Assessment, Primary Amyl Acetate, Dec. 23, 2014, p. 1-6.

\* cited by examiner

SHELF-STABLE HYDROGEN PEROXIDE ANTIMICROBIAL COMPOSITIONS

FIELD OF THE INVENTION

The present invention relates to peroxide containing antimicrobial compositions, e.g. disinfecting solutions.

BACKGROUND OF THE INVENTION

A wide range of disinfectants is known, as discussed for example in Disinfection, Sterilization, and Preservation, edited and partially written by Professor Seymour S. Block, Fifth Edition, published 2001 by Lippincott Williams & Wilkins, Philadelphia. Certain peroxygen compounds, chlorine compounds, phenolics, quaternary ammonium compounds and surface active agents are known for their germicidal properties. The rate of disinfection is relatively slow in many cases, and some compounds emit volatile organic compounds or leave a persistent and/or toxic residue in the environment.

Peroxide compounds, including hydrogen peroxide, are finding favour in many applications because their breakdown products, water and oxygen, are innocuous. Furthermore, they tend to have a broad spectrum of antimicrobial activity which is important in situations where harmful organisms are present but their identity is not known. However, even "broad spectrum" disinfectants may not be effective to kill all organisms or may harm the environment or user.

Formulating commercially viable hydrogen peroxide solutions is quite challenging. Desirable properties are often at odds with each other. For example, it is desirable to provide concentrated solutions that can be diluted by the end user prior to use, to save costs in terms of storage and transport. However, solutions containing 8% w/w or higher of hydrogen peroxide can be corrosive and hazardous to handle. On the other hand, solutions with lower hydrogen peroxide concentrations may be ineffective at high dilution ratios, e.g. at ratios of 1:40 or 1:64. Likewise, it is desirable to make solutions, that are antimicrobially-effective, low in toxicity, low in corrosiveness, biodegradable, and low in volatility. However, doing so can lead to instability of the peroxide in solution.

Therefore, a need still exists for a shelf-stable, commercially viable, hydrogen peroxide solution that is (at least) effective at high dilution ratios and environmentally-friendly.

SUMMARY OF THE INVENTION

The present invention provides concentrated and ready-to-use solutions, dry compositions for use in making said solutions, and methods of using the solutions and compositions.

In accordance with a first aspect, the invention provides a shelf-stable, concentrated antimicrobial solution, having a pH of from about 0 to about 3.5 and comprising, consisting essentially of, or consisting of:

a. hydrogen peroxide at a concentration of from about 1.5% w/w to 8% w/w;

b. at least one readily biodegradable anionic surfactant in a concentration of from about 10% w/w to about 30% w/w;

c. at least one of salicylic acid and salts thereof, in a concentration of from about 1% w/w to about 8% w/w;

d. at least one chelating agent in a concentration of from about 0.005% w/w to about 10% w/w;

e. at least one low-corrosive non-surfactant sulfonic acid selected from the group consisting of benzenesulfonic acid, benzene disulfonic acid, xylene sulfonic acid, toluene sulfonic acid, cumene sulfonic acid, sulfosalicylic acid, naphthalene mono- or di-sulfonic acid, and methane sulfonic acid, and isethionic acid in a concentration of from about 1% w/w to about 15% w/w;

f. optionally, at least one nonionic surfactant in a concentration of from about 1% w/w to about 15% w/w;

g. optionally, an effective amount of at least one additional ingredient selected from the group consisting of corrosion inhibitors, hydrotropes, dyes, defoamers, peroxide stabilizers, foam boosters, fragrances, pH adjusting agents, viscosity modifiers, soil suspenders, anti-redeposition agents, anti-freeze agents, solvents, additional strong acids, additional antimicrobial agents and diluents; and h. water q.s. to 100;

wherein the solution is substantially free of ingredients selected from the group consisting of peroxycarboxylic acids, acetic acid, furoic acid, phenylacetic acid, cationic surfactants, amphoteric surfactants, aromatic alcohols, halogen acids, phenols, peracid activators, bleaches, and (optionally) benzoic acid.

In some embodiments, the solution can include at least one glycol ether solvent in a concentration of from about 10% w/w to about 30% w/w. The glycol ether solvent can have a standard vapor pressure of less than 0.1 mm Hg.

The at least one readily biodegradable anionic surfactant can be chosen from the group comprising alkyl sulfonic acids, alkyl aryl sulfonic acids (e.g. e.g. C8 to C18 alkyl benzenesulfonic acids), alkyl sulfuric acids, sulfonated carboxylic acids, alkyl or alkenyl esters or diesters of sulfosuccinic acids, and alkali metal, ammonium, calcium and magnesium salts thereof. Preferably, the anionic surfactant is chosen from the group comprising alkyl sulfonic acids, alkyl aryl sulfonic acids (e.g. C8 to C18 alkyl benzenesulfonic acid), alkyl sulfates, and salts thereof.

In other embodiments, the solution is free of Volatile Organic Compounds (VOCs).

The solution can have a standard reduction potential (SRP) of from about 200, 250, 300, or 350 mV and up to about 400 mV.

The chelating agent can be selected from the group consisting of etidronic acid (1-hydroxyethane 1,1-diphosphonic acid or HEDP), N,N-bis(carboxymethyl) glutamic acid and salts thereof.

The at least one glycol ether solvent can be selected from the group consisting of tripropylene glycol methyl ether, tripropylene glycol n-butyl ether, polyethylene glycol phenyl ether, dipropylene glycol methyl ether, propylene glycol n-propyl ether, propylene glycol monomethyl ether, dipropylene glycol monopropyl ether, propylene glycol mono n-butyl ether, dipropylene glycol mono n-butyl ether, dipropylene glycol dimethyl ether, diethylene glycol monomethyl ether, diethylene glycol monoethyl ether, ethylene glycol monopropyl ether, ethylene glycol monobutyl ether, diethylene glycol monobutyl ether, ethylene glycol monohexyl ether, diethylene glycol monohexyl ether, and ethylene glycol phenyl ether.

The at least one non-surfactant sulfonic acid can be chosen from benzenesulfonic acid, naphthalene disulfonic acid, and toluene sulfonic acid.

The solution can have a pH adjuster (e.g. KOH, phosphoric acid) which is present in an amount effective to adjust the pH of the solution to the desired pH range.

According to a second aspect, the invention provides a ready-to-use disinfecting solution wherein the solution of the first aspect is diluted with a solvent, e.g. water, in a ratio of from about 1:2 to about 1:256, e.g. 1:2, 1:10, 1:16, 1:32, 1:64, 1:128, and 1:256. The pH of the diluted solution would be less than about 3.5.

Further to a third aspect, the invention provides a method for disinfecting a hard or soft surface, the method comprising applying to said hard or soft surface a solution according to the first or second aspect, wherein the solution provides at least a two-log reduction of bacteria at a maximum contact time of 5 minutes at a maximum 1:64 dilution using test method ASTM E1153. In some embodiments, the solution can provide at least a one log reduction of mycobacteria at a maximum contact time of 5 minutes at a maximum 1:40 dilution using test method AOAC 965.12. The present inventive solutions could also demonstrate antimicrobial activity against other microorganisms such as viruses, fungi, and bacterial spores.

The solutions according to the invention can be made from a kit of parts, wherein components of the solution (in dry or liquid form) are stored in separate containers, vessels, or packages. The user can combine the separate components to make concentrated or diluted ready-to-use solutions according to the invention. Dry compositions can also be formulated using dry forms of the ingredients used in the solution and combined with a liquid diluent, e.g. water and/or an organic solvent prior to use. For example, hydrogen peroxide can be supplied from solid sources, e.g. sodium perborate and sodium percarbonate.

The concentrated solutions, kits and dry compositions are more economical to transport and store relative to diluted, ready-to-use solutions. The present compositions and solutions are surprisingly effective against fungi, viruses and/or bacteria at high dilution ratios (e.g. 1:40 or 1:64). Embodiments of the inventive solutions are also safe to handle, surprisingly shelf-stable, and cause only low corrosion against soft metals, plastics and elastomers. Certain embodiments are also safe for the user (have low oral $LD_{50}$ toxicity, and low dermal and eye irritation), free of VOCs, readily biodegradable, and environmentally friendly.

The present inventive solutions form a single phase, clear solution, both at the time of formulation and upon dilution. Furthermore, following a freeze-thaw cycle, there is no irreversible phase separation or precipitation of ingredients. This allows the solutions to exhibit a consistent level of antimicrobial efficacy and maintain their aesthetic appeal to the end user.

The present invention contemplates the possibility of omitting any components whether or not they are recited herein and also of including components that fall within classes of compounds disclosed herein but which additional components may not be expressly recited.

BRIEF DESCRIPTION OF THE DRAWINGS

Embodiments of the invention will now be described with reference to the drawings in which.

DETAILED DESCRIPTION OF THE EMBODIMENTS

Figure 1:
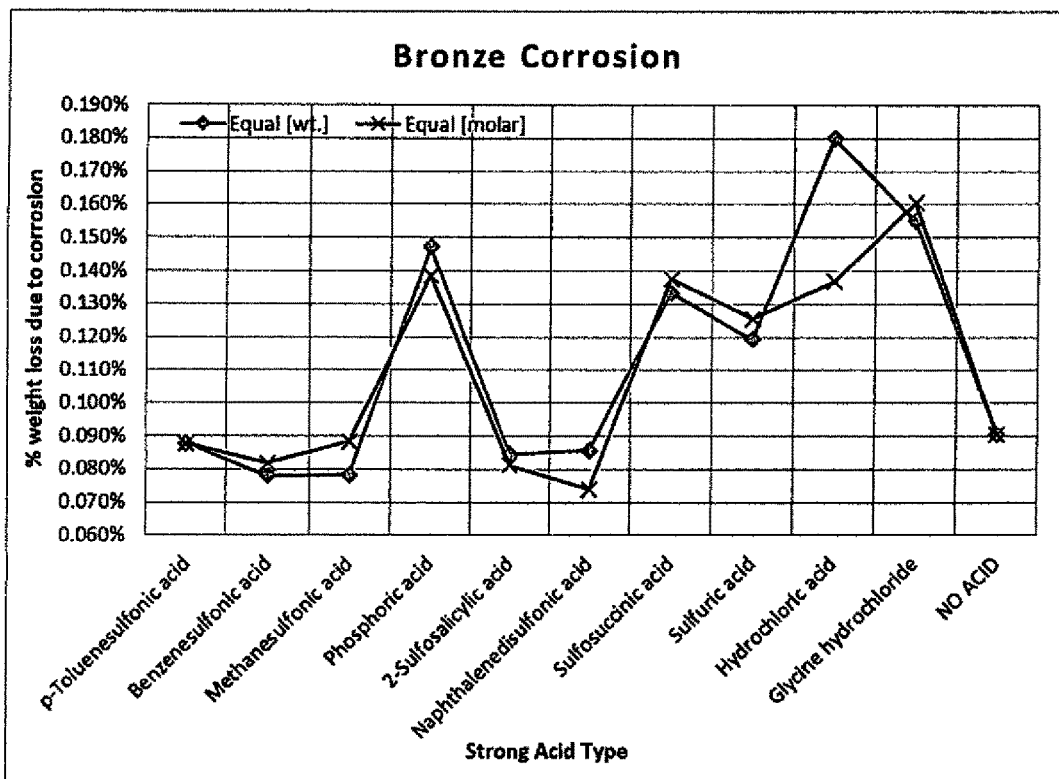
FIG. 1 is a graph depicting the results of corrosion tests using various solutions including solutions according to the invention.

To avoid ambiguity, certain terms are defined in the specification, as follows.

The term "comprising" means "including without limitation." Thus, a composition comprising a list of ingredients may include additional ingredients not expressly recited. The term "consisting of" means "including the listed ingredients and such additional ingredients as may be present as natural or commercial impurities or additives." Natural and commercial impurities will be apparent to the person of ordinary skill in the art. An example of a commercial additive is minute quantities of stabilizers in hydrogen peroxide commercial solutions. The term "consisting essentially of" means "consisting of the listed ingredients (as defined herein) plus such additional ingredients as would not materially affect (positively or negatively) the basic and novel properties of the solution." By "basic and novel properties" is meant the antimicrobial efficacy of the solution and shelf-stability as defined herein.

As used herein, the term "about" modifying the quantity of an ingredient in the compositions of the invention or employed in the methods of the invention refers to variations in the numerical quantity that can occur, for example, through typical measuring and liquid/solid handling procedures used for making concentrates or at-use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Solutions according to the invention are "shelf-stable." When used herein, a "shelf-stable" solution means a solution wherein the peroxide loss is no greater than about 5% when the solution is incubated at 54° C. for two weeks.

Surfactants are used in large amounts in commercial disinfectant cleaner solutions and can contribute to environmental pollution. The present invention employs surfactants that are "readily biodegradable." As defined herein, "readily biodegradable" when used in reference to a compound or substance means that 60-100% of the compound or substance will biodegrade when the substance is subjected to sunlight, water and microbial activity, for 28 days. "Inherently biodegradable" means that 20-60% of the compound or substance will biodegrade to its natural state, when subjected to sunlight, water and microbial activity within 28 days. The tests used to assess biodegradability are OECD Test Guideline 301A, 301B, 301C, 301D, 301E, 301F, and 310. As such, the present solutions are environmentally friendly.

As used herein, a composition or combination that is "substantially free of" one or more ingredients means a composition or combination that includes none of those ingredients or that includes only trace or incidental amounts of those ingredients. Trace or incidental amounts can include the amount of the ingredient found in another ingredient as an impurity or that is generated in a minor side reaction during formation or degradation of a component of the solution.

The solutions according to the invention can be formulated to not negatively impact indoor air quality. This can be done by omitting volatile organic compounds (VOCs) from the solution. When used herein, VOC means an organic compound having a vapor pressure 0.1 mmHg at an ambient room temperature of from about 20° C. to about 25° C. "Vapor pressure" means the pressure exerted by a vapor in thermodynamic equilibrium with its condensed phases (solid or liquid) at a given temperature in a closed system.

The higher the vapor pressure of a liquid at a given temperature, the higher the volatility and the lower the normal boiling point of the liquid. Embodiments of solutions according to the invention can have vapor pressures of less than about 0.12 mmHg, 0.11 mmHg, or 0.10 mmHg at an ambient room temperature of from about 20° C. to about 25° C.

The expression "oxidation/reduction potential" (ORP) is the tendency of a chemical species (e.g. a solution) to acquire electrons and thereby be reduced or release electrons and thereby be oxidized. Reduction potential is measured in volts (V), or millivolts (mV). Each solution has its own intrinsic reduction potential; the more positive the potential, the greater the solution's affinity for electrons and tendency to be reduced.

The term "standard reduction potential" is the oxidation/reduction potential measured under the following standard conditions: about 20° C. to 25° C., a partial pressure of 1 bar for each gas that is part of the reaction, and using metals in their relatively pure state (it being recognized that most metals are not available in a 100% pure state). The standard reduction potential is defined relative to a standard hydrogen electrode (SHE) reference electrode, which is arbitrarily given a potential of 0.00 volts.

As used herein, the term "corrosion" refers to a noticeable dissolution of metal surfaces or articles, which dissolution disfigures, modifies or otherwise causes interference with the intended functionality or appearance of the metal surface or article.

As used herein, the term "microorganism" refers to any noncellular or unicellular (including colonial) organism. Microorganisms include all prokaryotes. Microorganisms include bacteria (including cyanobacteria), lichens, yeasts, fungi, protozoa, virinos, viroids, viruses, phages, spores and some algae. As used herein, the term "microbe" is synonymous with microorganism.

"Hard surfaces" include but are not limited to glass, ceramics, metal, natural and synthetic rock, wood, and certain polymers, elastomers, and plastics. "Soft surfaces" include but are not limited to woven and non-woven substrates, a food product (and its surfaces); a body or stream of water or a gas (e.g., an air stream), the body of a living creature or part thereof, e.g. a human hand. Both hard and soft surfaces are encountered in the human and animal healthcare, hospitality, agriculture, food processing, and other industrial sectors.

The term "weight percent," "% w/w," "percent by weight," "% by weight," "% w/w," and variations thereof refer to the concentration of a substance as the weight of that substance divided by the total weight of the composition and multiplied by 100.

The term "effective amount" of a compound means that amount which provides the desired effect of the compound based on the compound's known function and properties as would be apparent to the person of ordinary skill in the art.

When used herein, a solution is "effective" against microorganisms, if the microbial populations are reduced by at least about 90% as compared to what is achieved by flushing with water or other antimicrobially inert solutions. Larger reductions in microbial population provide greater levels of protection.

Depending on the contact time and dilution rate employed, the present inventive solutions can function as a "sanitizer", disinfectant, sterilant, and/or sporicide. For example, when a 1:2 or 1:3 dilution rate is employed, embodiments of the invention can function as a sporicide at a contact time of less than 60 minutes.

As used herein, the term "sanitizer" refers to an agent that reduces the number of bacterial contaminants to safe levels as judged by public health requirements. In an embodiment, sanitizers for use in this invention will provide at least a 99.9% reduction (3-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2).

As used herein, the term "disinfectant" refers to an agent that kills most vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15th Edition, 1990 (EPA Guideline 91-2).

As used herein, the term "sterilant" refers to an agent that destroys all viable forms of microbial life. As used in this invention, the term "sporicide" refers to a physical or chemical agent or process having the ability to cause greater than a 90% reduction (1-log order reduction) in the population of spores of *Bacillus subtilis, Clostridium difficile,* or *Clostridium sporogenes* within 30 minutes at room temperature.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, biostatic. A sanitizer and a disinfectant are, by definition, agents which provide antimicrobial or microbiocidal activity. In contrast, a preservative is generally described as an inhibitor or biostatic composition.

In the description and claims, the singular forms "a," "an," and "the" include plural referents unless the content clearly dictates otherwise. Thus, for example, reference to a composition containing "a compound" includes a composition having two or more compounds. It should also be noted that the term "or" is generally employed in the sense of "and/or" unless the content clearly dictates otherwise.

Unless otherwise specified, the term "alkyl" or "alkyl group" refers to hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups or "cycloalkyl" or "alicyclic" or "carbocyclic" groups (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups, etc.).

Also, unless otherwise specified, the term "alkyl" includes both "unsubstituted alkyls" and "substituted alkyls." The term "substituted alkyls" refers to alkyl groups having substituents replacing one or more hydrogens on one or more carbons of the hydrocarbon backbone. Such substituents may include, for example, alkenyl, alkynyl, halogena, hydroxyl, alkylcarbonyloxy, arylcarbonyloxy, alkoxycarbonyloxy, aryloxy, a ryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonate, phosphine, cyano, amino (including alkyl amino, dialkylamino, arylamino, diarylamino, and alkylarylamino), acylamino (including alkylcarbonylamino, arylcarbonylamino, carbamoyl and uredo), amine, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including hetero aromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Hydrogen Peroxide

The present invention employs commercially available hydrogen peroxide stock solutions available from manufacturers such as Evonic and Arkema. The person skilled in the art will appreciate that such stock solutions will contain small amounts of proprietary stabilizers. As mentioned above, the present invention contemplates kits comprising separate components that can be added together by the final user and diluted with water to form a ready-to-use solution. In these cases, the hydrogen peroxide can be available in dry, powdered form. Suitable dry sources of hydrogen peroxide include, without limitation, sodium perborate, sodium percarbonate, urea peroxide, and persulfate derivatives.

The hydrogen peroxide is present in the concentrated solutions at a concentration of from about 1.5, 2, 2.5, 3, 3.5, 4, 4.5, 5, 5.5, and 6% w/w, and up to about 8, 7.5, 7, 6.5, 6, 5.5, 5, 4.5, and 4% w/w.

Readily Biodegradable Anionic Surfactants

Solutions according to the invention comprise at least one readily biodegradable anionic surfactant chosen from the group consisting of alkyl sulfonic acids, alkyl aryl sulfonic acids, alkyl sulfuric acids, sulfonated carboxylic acids, and alkyl or alkenyl esters or diesters of sulfosuccinic acids, and alkali metal, ammonium, calcium and magnesium salts thereof.

Exemplary alkyl aryl sulfonic acid would be C8-18 alkyl benzenesulfonic acid. Of the sulfonated carboxylic acids and their aforesaid salts, sulfonated 9-octadecanoic acid, disodium 2-sulfo C12-C18 fatty acid salts and sodium methyl-2-sulfo C12-C16 esters are exemplary. Exemplary alkali metal salts of alkyl sulfonic acids are sodium octyl (C8) sulfonate, sodium C14-C17 sec-alkyl sulfonate, and the sodium salts of 1-octane sulfonic acid, 1-decane sulfonic acid, and tridecane sulfonic acid. Of the aforesaid alkyl sulfates, sodium lauryl sulfate and sodium octyl sulfate are exemplary. Of the salts of alkyl or alkenyl esters or diesters of sulfosuccinic acid, disodium laureth sulfosuccinate and sodium dioctyl sulfosuccinate are exemplary.

The surfactants are used to enhance the solubility of the ingredients in the solution, the cleaning performance of the solution, and the permeation of antimicrobial actives such as hydrogen peroxide into microbial cells.

The anionic surfactant is present in the concentrated solutions at a concentration of from about 10, 12, 13, 14, 15, and 16% w/w to up to about 25, 22, 20, 19, 18, and 17% w/w.

Salicylic Acid and Salts Thereof

Solutions according to the invention will contain at least one of salicylic acid and salts thereof. The salicylic acid functions to enhance the microbicidal efficacy of the solution. These compounds are present in the concentrated solutions at a concentration of from about 1, 1.5, 2, 3, 4, and 5% w/w and up to about 8, 7, 6, and 5% w/w.

Chelating Agents

The present solution employs at least one chelating agent which contributes to the stability of the hydrogen peroxide in solution by forming complexes with and thereby removing metal ions from solution. Examples that can be used in the context of the present invention include phosphoric acid, sodium stannate, ethylene diamine tetraacetic acid (EDTA), 2-hydroxyethyl ethylenediaminetriacetic acid (HEDTA), tertiary amine-based chelating agents, and phosphonate-based chelating agents, and salts thereof. The tertiary amine-based chelating agent includes at least one tertiary amine group in each molecule. Examples of tertiary amine-based chelating agents include L-glutamic acid N,N-diacetic acid (GLDA), methylglycine diacetic acid (MGDA), diethylenetriaminepentaacetic acid (also referred to as pentetic acid or DTPA), and nitrilotriacetic acid (NTA). The phosphonate-based chelating agent employed herein contains at least one phosphonate or phosphonic acid group in each molecule. Examples include 1-hydroxyethane-1,1-diphosphonic acid (HEDP or etidronic acid), aminotrimethylene phosphonic acid (ATMP), di-ethylene tri-amine pentakis methylenephosphonic acid (DTPMP), ethylene di-amine tetrakis methylenephosphonic acid (EDTMP), hexamethylenediaminetetrakis methylenephosphonic acid (HDTMP), cyclohexane-1,2-tetramethylene phosphonic acid, 2-phosphonobutane-1,2,4-tricarboxylic acid (PBTC), and salts thereof. Exemplary salts include alkali metal salts, ammonium salts, alkyloyl amine salts (e.g. mono, di, or tetra-ethanolamine salts). The skilled person will appreciate that certain chelating agents, e.g. phosphoric acid and most phosphonate-based chelating agents in their acid form, also function as a "strong acid" as defined herein.

The at least one chelating agent is present in the concentrated solutions at a concentration of from about 0.005, 0.01, 0.1, 0.5, 1, 1.5, 2, 4, or 8% w/w or up to about 10, 9, 7.5, 6, 5, 3, or 2.5% w/w.

Non-Surfactant Sulfonic Acids and Solution pH

The concentrated solutions according to the invention will have a pH ranging from about 0, 0.5, 1.5 to about 2. Diluted, ready-to-use versions of solutions according to the invention will have pH values ranging from about 1.6 to about 3.5. These pH ranges are required for optimal antimicrobial efficacy. To achieve the desired end-use pH of diluted solutions, the invention employs at least one strong acid. As used herein, the term "strong acid" refers to those acids with pKa values ≤ about 2. Preferably, the at least one strong acid is selected from non-surfactant sulfonic acids, such as benzenesulfonic acid, benzene disulfonic acid, xylene sulfonic acid, toluene sulfonic acid, cumene sulfonic acid, sulfosalicylic acid, naphthalene mono- or di-sulfonic acid, methane sulfonic acid, sulfosuccinic acid, and isethionic acid. When used herein, non-surfactant sulfonic acids are sulfonic acids containing 10 or fewer carbon atoms in their molecules and four or fewer carbon atoms in a linear or branched chain component of the molecule. The carbonic component of the molecule could be substituted, unsubstituted, saturated or unsaturated. Non-surfactant sulfonic acids are preferred over other strong acids, such as nitric acid, sulfuric acid, and hydrochloric acid, as they are considered less harmful to users and to the environment. Surprisingly, some of these non-surfactant sulfonic acids (shown in FIG. 1) do not increase the corrosiveness of the solution.

The at least one non-surfactant sulfonic acid is present in concentrated versions of the solution at a concentration of from about 0.5, 1, 2, 3, 4, 5, 6 and 7% w/w and up to about 15, 14, 13 12, 11, 10, 9, 8, 8, 7, and 6% w/w.

Dry Compositions and Ready-to-Use Versions

The present invention provides compositions that can be in liquid or dry form. When in liquid form, the solution will comprise a liquid diluent, i.e. water (Q.S. to 100) and, optionally, an organic solvent. When in dry form, the water and solvent are omitted and the remaining ingredients will be present as dry versions thereof. The skilled person will appreciate what forms of compounds in dry form can be combined with a liquid diluent to produce a solution according to the invention (whether concentrated or ready-to-use).

In certain embodiments, the present solution includes water in an amount of from about 25, 30, 35, 40, 45, 50, 65, 75, 85, and 90% w/w, and up to about 99.8, 99, 97, 95, 93, 90 and 85% w/w. For example, in certain embodiments, the present solution can include about 30, 40, 50, 60, 70, 75, 80, 85, 90, 95, 98 or 99.5% w/w water. It will be appreciated that concentrated versions of the solution will have less water than ready-to-use versions.

The diluent provides a medium which dissolves, suspends, or carries the other components of the composition or solution. For example, the diluent can provide a medium for solubilization, suspension, or production of the composition or solution. The diluent can also function to deliver and wet the antimicrobial solution of the invention on an object. To this end, the diluent can contain any component or components that can facilitate these functions.

Exemplary non-aqueous diluents include glycol ethers and polyols. Examples of glycol ethers are diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, propylene glycol monomethyl ether, propylene glycol mono n-butyl ether, diethylene glycol mono-methyl ether, diethylene glycol monoethyl ether, dipropylene glycol dimethyl ether, dipropylene glycol monopropyl ether, dipropylene glycol mono n-butyl ether, tripropylene glycol methyl ether and tripropylene glycol n-butyl ether, ethylene glycol monopropyl ether, ethylene glycol monobutyl ether, ethylene glycol monohexyl ether, diethylene glycol monobutyl ether, diethylene glycol monohexyl ether, polyethylene glycol phenyl ether, ethylene glycol phenyl ether (commercially available as DOWANOL EPH from Dow Chemical Co.), propylene glycol phenyl ether (commercially available as DOWANOL PPH from Dow Chemical Co.), and the like, or mixtures thereof. Additional suitable commercially available glycol ethers (all of which are available from Union Carbide Corp.) include butoxyethyl PROPASOL, Butyl CARBITOL acetate, Butyl CARBITOL, Butyl CELLOSOLVE acetate, Butyl CELLOSOLVE, Butyl DIPROPASOL, Butyl PROPASOL, CARBITOL PM-600, CARBITOL Low Gravity, CELLOSOLVE acetate, CELLOSOLVE, Ester EEP, FILMER IBT, Hexyl CARBITOL, Hexyl CELLOSOLVE, Methyl CARBITOL, Methyl CELLOSOLVE acetate, Methyl CELLOSOLVE, Methyl DIPROPASOL, Methyl PROPASOL acetate, Methyl PROPASOL, Propyl CARBITOL, Propyl CELLOSOLVE, Propyl DIPROPASOL and Propyl PROPASOL. Examples of polyols are glycerol, sorbitol, and the like.

Other solvents that can be used are methanol, ethanol, butyl 3-hydroxybutyrate, isopropyl alcohol, ethylhexylglycerol, branched or unbranched diols, charged or uncharged non-surfactant emulsifying agents, dibasic esters, polar protic solvents, polar aprotic solvents (e.g. glycerine carbonate), and mixtures thereof.

Concentrated solutions according to the invention preferably comprise at least one glycol ether solvent to enhance the solubility of ingredients (e.g., salicylic acid) in solution, and enhance cleaning efficacy against organic or inorganic soils. Examples include methoxytriglycol, ethoxytriglycol, butoxytriglycol, hexyltriglycol, propylene glycol methyl ether acetate, dipropylene glycol methyl ether acetate, dipropylene glycol n-butyl ether, propylene glycol n-butyl ether, dipropylene glycol n-propyl ether, propylene glycol n-propyl ether, dipropylene glycol methyl ether, and tripropylene glycol methyl ether. Glycol ethers with a standard vapor pressure of less than about 0.1 mmHg would not be considered VOCs.

In concentrated solutions, the glycol ether solvent can be present in a concentration of from about 10, 12, 14, 16, and 18% w/w and up to about 30, 25, 23, 21, 19, and 17% w/w.

Other Optional Ingredients

The solutions according to the invention can include additional optional ingredients as follows.

Nonionic Surfactants

The solution can further comprise at least one nonionic surfactant. Suitable nonionic surfactants include a surfactant with ethylene oxide moieties, propylene oxide moieties or mixtures thereof, and surfactants with ethylene oxide-propylene oxide moieties in heteric, block or random hetericblock formation (e.g. block copolymers). Examples include alkyl ethylene oxide surfactants, alkyl propylene oxide surfactants, and alkyl ethylene oxide-propylene oxide surfactants. The nonionic surfactants can be a nonionic surfactant having any mixture or combination of ethylene oxide-propylene oxide moieties linked to an alkyl chain where the ethylene oxide and propylene oxide moieties may be in any randomized or ordered pattern and of any specific length. Nonionic moieties may be capped/terminated with a benzyl, alkoxy or short chain alkyl grouping.

The nonionic surfactants can be a condensation product of a saturated or unsaturated, straight or branched chain alcohol having from about 6 to 24 carbon atoms with about 3 to about 50 moles of ethylene oxide (i.e. alcohol ethoxylates). The alcohol moiety can consist of mixtures of alcohols in the above delineated carbon range or it can consist of an alcohol having a specific number of carbon atoms within this range. Examples of commercial surfactants of this chemistry are available under the trade name of Surfonic manufactured by Huntsman Corp., Austin, Tex., Pluronic manufactured by BASF Corp., Florham Park, N.J., and Neodol manufactured by Shell Chemical Co., Houston, Tex.

Other useful nonionics are alkyl glucosides and alkyl polyglucosides.

The at least one nonionic surfactant can be present from at least about 0.5, 1, 1.5, 2, 2.5, 5, 8, and 10% w/w, and up to about 30, 25, 20, 15, 12, 10, 8, and 7% w/w.

Corrosion Inhibitors

The solution of the present invention can include at least one corrosion inhibitor. Suitable corrosion inhibitors include triazoles, such as benzotriazole or tolytriazole. Other corrosion inhibitors include molybdate salts and zinc dithiophosphate. The corrosion inhibitor can be present in concentrated solutions in an amount starting from about 0.1, 0.5, 1, 5, and 10% w/w, and up to about 15, 7, and 3% w/w.

Hydrotropes

The solution of the invention may include one or more hydrotropes, some of which can also be the non-surfactant sulfonic acids discussed above. The hydrotropes include but are not limited to aryl and alkylaryl sulfonic acids such as xylene sulfonic acid, cumene sulfonic acid, toluene sulfonic acid and their salts, polyether phosphate esters, and diphenyloxide disulfonates. These ingredients are useful for increasing the miscibility or solubility of organic and inorganic materials to produce a phase-stable aqueous solution. Hydrotropes can also help with cleaning organic soils.

When used in concentrated solutions, the hydrotrope can be present in an amount from about 0.1, 1, 3, 5, 10, and 20% w/w, and up to about 25, 15, 8, 4, 1.5, and 0.5% w/w.

Additional Peroxide Stabilizers

The solutions may include an effective amount of an additional peroxide stabilizer including, without limitation, 2-hydroxyethyliminodiacetic acid (HEIDA), aminobenzoic acid, acetanilide, phytic acid, citric acid, iminodisuccinic acid, polyaspartic acid, tripolyphosphate, and salts thereof.

Additional Strong Acids

The present invention can employ additional strong acids for achieving the desired pH when the solutions are diluted for use. As used herein, the term "strong acid" refers to those acids with pKa values ≤ about 2. Examples of additional strong acids that can be used are mineral acids such as sulfuric acid, phosphoric acid, nitric acid, and hydrochloric acid.

pH Adjusting Agents and Buffers

The solutions can include an effective amount of pH adjusting agents (also referred to herein as pH adjusters) to adjust the pH of the solutions to the desired value. Examples of alkaline pH adjusting agents in accordance with the invention include potassium hydroxide (KOH), sodium hydroxide (NaOH), lithium hydroxide, magnesium hydroxide, calcium hydroxide, rubidium hydroxide, cesium hydroxide, strontium hydroxide and barium hydroxide. Buffers can also be employed to maintain the pH within the desired range.

Additional Antimicrobial Compounds

In some embodiments, the solution may include an additional antimicrobial compound (e.g. sanitizing or disinfecting agent) for killing microbes and the like. The antimicrobial compound may be chosen from amine oxide surfactants, essential oils, organic acids, parabens, aldehydes (e.g. formaldehyde), phenols, alcohols, biguanides, formaldehyde releasing agents, and/or mixtures thereof, other than those compounds that are expressly excluded from the scope of the invention described herein.

When used, the concentration of the additional antimicrobial compound in concentrated solutions may be from about 0.005, 0.1, 1, 5, 10, 20, or 40% w/w, and up to about 50, 30, 15, 3, or 0.5% w/w.

Additional Ingredients

The present inventive solutions may include additional ingredients as would be apparent to the person skilled in the art, including without limitation, wetting agents, pigments and dyes, foaming and defoaming agents (e.g. aliphatic acids or esters; alcohols; vegetable oils, waxes, mineral oils as well as their sulfated derivatives, silicones, such as dimethyl silicone, glycol polysiloxane, methylphenol polysiloxane, trialkyl or tetraalkyl silanes, and hydrophobic silica defoamers), softening agents, anti-static agents, dye transfer inhibition/color protection agents, odor removal/odor capturing agents, builders, brighteners, preservatives, ultraviolet light protection agents, water repellency agents, allergicides, soil suspenders, anti-redeposition agents, antifreeze agents, and mixtures thereof. The solutions of the invention can also contain any number of other constituents as necessitated by the application, which are known and which can facilitate the activity of the present invention. Such additional ingredients can be preformulated with the antimicrobial solution of the invention or added to the solution prior to use.

Methods Employing the Present Antimicrobial Solutions

The invention includes methods employing the present antimicrobial solutions. For example, the invention includes a method for reducing a microbial population on a hard or soft surface, a method for reducing the population of a microorganism on skin, a method for treating a disease of skin, or a method for reducing an odor. A concentrate or use concentration of a solution of the present invention can be applied to or brought into contact with an object by any conventional method or apparatus for applying an antimicrobial or cleaning solution to the object. Contacting can include any of numerous methods for applying a solution such as spraying the solution, impregnating the solution in wipes (woven or non-woven textile material) and using the wipes to wipe down a surface to be treated, immersing an object in the solution, foam or gel treating an object with the solution, misting and fogging, or a combination thereof. The solution can also be caused to flow over the surface, or the surface can be dipped into the solution. Contacting can be manual or by machine.

The solutions of the invention can be used for a variety of domestic (e.g. residential) or industrial (e.g. commercial, institutional) applications. The solutions can be applied in a variety of areas including kitchens, bathrooms, factories, hospitals, dental offices and food plants. The antimicrobial solutions can also be used in veterinary products such as mammalian skin treatments or in products for sanitizing or disinfecting animal enclosures, watering stations, and veterinary treatment areas such as inspection tables and operating rooms. The present solutions can be employed in an antimicrobial foot bath for livestock or as a boot or shoe sole dip for people.

Suitable hard surfaces that can be treated with solutions according to the invention include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood, or hard plastic. Suitable soft surfaces include, for example fabrics, filter media, hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The solutions of the invention can also be applied to soft surfaces such as food and skin (e.g., a hand). The present solutions can be employed as a foaming or non-foaming environmental sanitizer or disinfectant.

The antimicrobial solutions of the invention can be included in products such as sterilants, sanitizers, disinfectants, preservatives, deodorizers, antiseptics, fungicides, germicides, sporicides, virucides, detergents and hard and soft surface cleaners. The solutions can exhibit activity against pathogens including fungi, molds, bacteria, spores, and viruses, for example, Trycophyton sp., *Aspergillus* sp., *Staphylococcus* sp., antibiotic resistant *Staphylococcus* sp., *E. coli, Streptococcus* sp., *Enterococcus* sp., *Legionella* sp., *Pseudomonas* sp., *Mycobacterium* sp., *Clostridium* sp., influenza and hepatitis viruses, phages, and the like. Such pathogens can cause a variety of diseases and disorders, including tuberculosis, lung and tissue infections, septicemic infections, hemolytic gastroenteritis, influenza, hepatitis, and the like. The solutions of the present invention can reduce the population of microorganisms on skin or other external or mucosal surfaces of an animal.

The antimicrobial solutions can also be used on foods and plant species to reduce surface microbial populations, and/or used at manufacturing or processing sites handling such foods and plant species. For example, the solutions can be used on food transport lines (e.g., as belt sprays); boot and hand-wash dip-pans; food storage facilities; refrigeration and cooler equipment; beverage chillers and warmers, blanchers, cutting boards, third sink areas, and meat chillers or scalding devices. Foodstuffs that can be treated with solutions of the invention include eggs, seeds, leaves, fruits and vegetables. Plant surfaces include both harvested and growing leaves, roots, seeds, skins or shells, stems, stalks, tubers, corn, fruit, and the like.

Solutions according to the invention are useful at all temperature ranges, i.e. from about −30° C. to about 80° C. It is expected that at higher temperatures, antimicrobial contact times can be reduced.

The present invention may be better understood with reference to the following examples. These examples are intended to be representative of specific embodiments of the invention, and are not intended as limiting the scope of the invention.

EXAMPLES

Solutions were prepared using the ingredients listed in Table A below and tested for hydrogen peroxide stability.

TABLE A

| Classification | Ingredient Identity_Brand Name_Commercial Source (% w/w/ active) |
| --- | --- |
| Anionic Surfactant - Readily Biodegradable | Alkyl (C10-16) benzenesulfonic acid_Bio-Soft S-101_Stepan (96% w/w active) |
| Anionic Surfactant - Inherently Biodegradable | Mono/di-alkyl (C10) diphenyloxide disulfonate_Dowfax C10L_Dow Chemicals (45% w/w active) |
| Cyclic Carboxylic Acid | Salicylic acid_N/A_Sigma Aldrich (≥99% w/w active) |
| | 2-Furoic acid_N/A_PennAKem (95-100% w/w active) |
| | Phenylacetic acid_N/A_Sigma Aldrich (99% w/w active) |
| Peroxide Source | Hydrogen Peroxide_Peroxal ® 50 BIO_Arkema (50% w/w active) |
| Nonionic Surfactant | Polyoxypropylene-polyethylene block copolymer_Pluronic L62_BASF Corporation (100% w/w active) |
| | Alcohols, C9-11, ethoxylated (EO = 2.5)_Tomadol 91-2.5_Air Products (100% w/w active) |
| | Alcohols, C9-11, ethoxylated (EO = 6)_Tomadol 91-6_Air Products (100% w/w active) |
| Non-surfactant Sulfonic Acid | p-Toluene sulfonic acid, monohydrate_N/A_Sigma Aldrich (≥98.5% w/w active) |
| | Benzenesulfonic acid_N/A_Sigma Aldrich (98% w/w active) |
| | Methane sulfonic acid_Lutropur MSA 100_BASF Corporation (≥99% w/w active) |
| | 5-Sulfosalicylic acid dihydrate_N/A_Sigma Aldrich (≥99% w/w active) |
| Tertiary amine-based or phosphonate-based chelating agent | Etidronic acid_Dequest 2010_Italmatch Chemicals (60% w/w active) |
| | L-glutamic acid N,N-diacetic acid, tetrasodium salt_AkzoNobel_Dissolvine GL-47-S (48% w/w active) |
| Glycol Ether Solvent | Dipropylene glycol methyl ether_Dowanol DPM_Dow Chemicals (>99% w/w active) |
| | Tripropylene glycol methyl ether_Dowanol TPM_Dow Chemicals (≥97.5% w/w active) |
| | Tripropylene glycol n-butyl ether_Dowanol TPnB_Dow Chemicals (≥95% w/w active) |
| | Propylene glycol n-propyl ether_Dowanol PnP_Dow Chemicals (>99% w/w active) |
| | Propylene glycol n-butyl ether_Dowanol PnB_Dow Chemicals (>95% w/w active) |
| Aromatic Alcohol | Benzyl alcohol_N/A_INEOS (100% w/w active) |
| Corrosion Inhibitor | Benzotriazole_N/A_Cobratec 35G_PMC Specialties Group (35% w/w active) |
| Antifoaming Agent | Siloxane-silica based defoamer_XFO-964_Ivanhoe Industries |
| pH Adjusting Agent | Potassium hydroxide_N/A_Sigma Aldrich (45% w/w active) |
| | Phosphoric acid_N/A_Sigma Aldrich (75% w/w active) |
| Polar Aprotic Solvent | Glycerine carbonate_N/A_Sigma Aldrich |
| Diluent/Base Carrier | Deionized Water |

Hydrogen peroxide stability was measured in terms of the % loss of hydrogen peroxide in a solution incubated at 54° C. for a period of two weeks. The concentration of hydrogen peroxide before and after the two week period was measured using a standard colorimetric iodine based titration method employing sodium thiosulfate. As defined above, a "shelf-stable" solution is one in which no more than about 5% of hydrogen peroxide was lost under the conditions of the test.

The results are summarized in Tables 1 and 2 below. In these tables, the amount of each raw material is shown in terms of % w/w based on the total weight of the solution. The actual concentration of an ingredient can be calculated by multiplying the concentration of the ingredient in the raw material by the concentration shown in the tables. For example, in Table 1, the amount of etidronic acid in solution C is 60%×0.5% w/w=0.3% w/w. Where no concentration is listed for the starting raw material, the concentration of the ingredient in the raw material is about 100%. For example, solution A contains 3% w/w of polyoxypropylene-polyethylene block copolymer, i.e. 100%×3% w/w=3% w/w.

Example 1

Hydrogen Peroxide Stability Tests

Solutions A-J are not in accordance with the invention and are summarized in Table 1 below.

The results shown in Table 1 above, when compared with the results shown in Table 2 below, highlight the surprising improvement in stability resulting from the non-routine adjustment and selection of ingredients. None of the solutions in Table 1 are "shelf-stable" as herein defined. All solutions A-J contain hydrogen peroxide in a concentration of from about 6.6 to about 7.1% w/w, at least one readily biodegradable anionic surfactant (alkyl (C10-16) benzenesulfonic acid) in a concentration of from about 10-20% w/w, and a nonionic surfactant (polyoxypropylene-polyethylene block copolymer) in a concentration of from about 2.5-5% w/w.

Solutions A, B, E, G, H and J do not contain at least one chelating agent according to the present invention. Solution F does not contain at least one of salicylic acid and salt thereof. Solutions B, D, E, G, H and J do not contain at least one non-surfactant sulfonic acid according to the invention (e.g. methane sulfonic acid). Solutions C, F, and I include ingredients that are excluded from the scope of the invention, namely, phenylacetic acid, furoic acid and benzyl alcohol respectively.

Solution B contains an example of an anionic surfactant that is not readily biodegradable, namely, Mono/di-alkyl (C10) diphenyloxide disulfonate. Therefore, Solution B is not environmentally favourable.

Solutions K-U are in accordance with the invention and summarized in Table 2 below.

TABLE 1

| Solution | A | B | C | D | E | F | G | H | I | J |
|---|---|---|---|---|---|---|---|---|---|---|
| Water | QS 100 | QS 100 | QS 100 | QS 100 | QS 100 | QS 100 | QS 100 | QS 100 | QS 100 | QS 100 |
| Polyoxypropylene-polyethylene block copolymer | 3 | 5 | 2.5 | 3 | 5 | 2.5 | 5 | 5 | 2.5 | 5 |
| Alkyl (C10-16) benzenesulfonic acid (96% w/w) | 18 | 10 | 15 | 15 | 12 | 17 | 12 | 10 | 20 | 10 |
| Salicylic acid | 3.3 | 2.5 | 2.8 | 3.5 | 1.8 | — | 1.8 | 2.5 | 2.8 | 2.5 |
| Alcohols, C9-11, ethoxylated (EO = 2.5) | — | — | 1 | 2 | — | 1 | — | — | 1 | — |
| Alcohols, C9-11, ethoxylated (EO = 6) | — | — | 0.8 | — | — | 0.8 | — | — | 0.8 | — |
| Dipropylene glycol methyl ether | 17 | — | 11 | 15 | 10.2 | 7 | — | — | 13.5 | — |
| Propylene glycol n-propyl ether | — | 8 | — | — | — | — | — | 8 | — | 8 |
| Propylene glycol n-butyl ether | — | — | — | — | — | — | 10.2 | — | — | — |
| Benzotriazole (35% w/w) | — | — | — | — | — | 0.2 | — | — | — | — |
| Methane sulfonic acid | 2.8 | — | 2.82 | — | — | 2.82 | — | — | 2.8 | — |
| Mono/di-alkyl (C10) diphenyl oxide disulfonate (45% w/w) | — | 10 | — | — | — | — | — | — | — | — |
| Phosphoric acid (75% w/w) | — | — | — | — | — | — | — | — | — | 9 |
| Etidronic acid (60% w/w) | — | — | 0.5 | 0.5 | — | 1 | — | — | 0.5 | — |
| Benzyl alcohol | — | — | — | — | — | — | — | — | 2 | — |
| Furoic acid | — | — | — | — | — | 2 | — | — | — | — |
| Phenylacetic acid | — | — | 2 | — | — | — | — | — | — | — |
| Potassium hydroxide (45% w/w) | — | — | — | — | — | 0.2 | — | — | — | — |
| Hydrogen peroxide (50% w/w) | 15 | 15 | 15 | 13.2 | 14 | 15.2 | 14 | 15 | 14.4 | 15 |
| pH | −0.18 | 0.20 | 0.17 | 0.33 | 0.45 | 0.42 | 0.43 | 0.18 | 0.01 | 0.11 |
| Hydrogen peroxide loss (%) after 2 weeks at 54° C. | 88.6 | 16.2 | 15.5 | 9.8 | 34.7 | 17.6 | 26.2 | 15.9 | 7.2 | 14.8 |

TABLE 2

| Solution | K | L | M | N | O | P | Q | R | S | T | U |
|---|---|---|---|---|---|---|---|---|---|---|---|
| Water | QS to 100 | QS to 100 | QS to 100 | QS to 100 | QS to 100 | QS to 100 | QS to 100 | QS to 100 | QS to 100 | QS to 100 | QS to 100 |
| Polyoxypropylene-polyethylene block copolymer | 3 | 2.5 | 2.5 | 3 | 2.5 | 3 | 2.5 | 3 | 2.5 | 3 | — |
| Alkyl (C10-16) benzenesulfonic acid (96% w/w) | 17.5 | 17 | 15 | 17.5 | 17 | 18 | 15 | 17 | 20 | 17 | 17 |
| Salicylic acid | 4 | 3.3 | 3.3 | 4 | 3.3 | 3.3 | 2.8 | 4 | 2.8 | 4 | 4 |
| Alcohols, C9-11, ethoxylated (EO = 2.5) | 1 | 1 | 1 | 1 | 1 | — | 1 | 1 | 1 | 1 | — |
| Alcohols, C9-11, ethoxylated (EO = 6) | 1 | 0.8 | 0.8 | 1 | 0.8 | — | 0.8 | 1 | 0.8 | 1 | — |
| Dipropylene glycol methyl ether | — | — | 11 | — | 17 | 17 | 13.5 | — | 13.5 | — | — |
| Tripropylene glycol methyl ether | 17.25 | 11 | — | 17.25 | — | — | — | 17.3 | — | 17.3 | 17.3 |
| Tripropylene glycol n-butyl ether | — | — | — | — | — | — | — | — | — | — | 5 |
| Benzotriazole (35% w/w) | — | 0.2 | 0.3 | — | 0.2 | — | — | — | — | — | — |
| Glycerine carbonate | 0.5 | — | — | — | — | — | — | — | — | 0.4 | — |
| p-Toluene sulfonic acid, monohydrate | 3.6 | — | — | — | — | — | — | 3.6 | — | 6 | 3.6 |
| Benzenesulfonic acid | — | — | — | 3.4 | — | — | — | — | — | — | — |
| Methane sulfonic acid | — | 3 | 3 | — | 3 | 2.1 | 3 | — | 2.8 | — | — |
| Phosphoric acid (75% w/w) | — | — | — | — | — | — | 3 | — | — | — | — |
| 5-Sulfosalicylic acid | — | — | — | — | 5 | — | — | — | — | — | — |
| Etidronic acid (60% w/w) | 1 | 1 | 1 | 0.7 | 1 | 0.5 | 1 | 1.2 | 0.5 | 1 | 1 |
| L-glutamic acid N,N-diacetic acid, tetrasodium salt (48% w/w) | — | — | 0.05 | — | — | — | 0.05 | — | 0.05 | — | — |
| Siloxane-silica based defoamer | 2 | — | — | — | — | — | — | — | — | — | — |
| Potassium hydroxide (45% w/w) | 0.2 | 0.2 | 0.2 | 0.14 | 0.2 | 0.1 | 0.2 | 0.24 | — | 0.2 | 0.2 |
| Hydrogen peroxide (50% w/w) | 14 | 15.2 | 15 | 15.2 | 15.2 | 15 | 14.4 | 14 | 14.4 | 14 | 14 |
| pH | 0.05 | 0.28 | 0.08 | 0.10 | 0.35 | 0.35 | 0.20 | 0.09 | 0.05 | 0.01 | 0.08 |
| Hydrogen peroxide loss (%) after 2 weeks at 54° C. | 4.5 | 3.8 | 4.5 | 4.1 | 3.9 | 2.3 | 4.8 | 3.1 | 5.1 | 4.5 | 4.1 |

All solutions K-R contain (a)

a. hydrogen peroxide in a concentration of from about 7 to about 7.6% w/w;

b. at least one readily biodegradable anionic surfactant (alkyl (C10-16) benzenesulfonic acid) in a concentration of from about 15 to about 20% w/w;

c. a chelating agent (etidronic acid alone or in combination with acetanilide) in a concentration of from about 0.3 to about 0.72% w/w;

d. salicylic acid in a concentration of from about 2.8 to about 4% w/w;

e. at least one glycol ether solvent (dipropylene glycol methyl ether, tripropylene glycol methyl ether, and/or tripropylene glycol n-butyl ether), in a concentration of from about 11 to about 22.3% w/w;

f. at least one non-surfactant sulfonic acid selected from the group consisting of benzenesulfonic acid, toluene sulfonic acid, sulfosalicylic acid, and methane sulfonic acid in a concentration of from about 2.1 to about 6% w/w; and g. the balance, water.

Solutions K-T also comprise an optional nonionic surfactant (block copolymer and alcohol ethoxylates) in a concentration of from about 3 to about 5% w/w. A perusal of the solutions in Table 2 will show the presence of additional optional ingredients in selected solutions (corrosion inhibitor—benzotriazole; antifoaming agent—siloxane-silica based defoamer; pH adjusting agent—phosphoric acid; and polar aprotic solvent—glycerine carbonate)

None of solutions K-U include ingredients outside the scope of the invention, namely, acetic acid, furoic acid, phenylacetic acid, cationic surfactants, amphoteric surfactants, aromatic alcohols, halogen acids, phenols, peracid activators, and bleaches.

All Solutions K-U are "shelf-stable" as the term is defined herein. Solutions K, N, R and U are less corrosive than the other solutions in Table 2 and are preferred where low corrosion is desired.

Antimicrobial Tests

Solutions Q, S and R above were tested for their antimicrobial efficacy using test methods AOAC 955.15, ASTM E1153, and AOAC 965.12. The tests and results are summarized in Table 3 below. Results expressed in terms of "log reduction" refer to the log reduction compared to the original microbial titer's population.

TABLE 3

| | Solution | | | |
|---|---|---|---|---|
| | Q (at 1:40 dilution) | S (at 1:40 dilution) | R (at 1:40 dilution) | |
| Test Method | AOAC 955.15 | AOAC 955.15 | ASTM E1153 | AOAC 965.12 |
| Test Organism | S. aureus | S. aureus | S. aureus | M. terrae |
| Contact Time | 5 mins | 5 mins | 30 sec | 5 mins |
| Test Result | 3 growths out of 60 | 5 growths out of 60 | 99.70% reduction | >4.43 log reduction |

Solutions Q and S at a 1:40 dilution were able to inactivate more than 90% of the bacterial test carriers using the AOAC 955.15 disinfection test method at a 5-minute exposure time at room temperature. Solution R was able to reduce more than 90% of the bacterial population using the ASTM E1153 test method at a 30 second exposure time at room temperature. Solution R was also able to reduce the mycobacterial population by at least 3 logs at a 5-minute exposure time at room temperature using test method AOAC 965.12.

Solution R at a 1:2 dilution was also tested against bacterial spores of $B.\ subtilis$ at a contact time of 30 minutes using the ASTM E2167 method. The diluted solution contained hydrogen peroxide at about 2.33% w/w. and was able to reduce the population of $B.\ subtilis$ spores by 5.5 logs. Surprisingly, the tested solution performed far better than the claimed sporicidal activity of a competing sporicidal product sold in association with the trademark Revital-Ox™ RESERT® High Level Disinfectant-Chemosterilant by STERIS Corporation. The Revital-Ox™ RESERT® brand product contains about 2% w/w hydrogen peroxide and claims to require a contact time of 6 hours to achieve a similar level of sporicidal activity.

Metal Corrosion

FIG. 1 depicts the results of corrosion tests of various solutions.

A base solution which does not contain a non-surfactant sulfonic acid according to the invention was prepared and referred to as NO ACID in FIG. 1. The NO ACID solution was made using 15% w/w of alkyl (C10-16) benzenesulfonic acid, 2% w/w of C9-11 ethoxylated alcohol with EO=6, 3.5% w/w of salicylic acid, 16% w/w of tripropylene glycol methyl ether, 0.6% w/w of etidronic acid, 6% w/w of hydrogen peroxide, and the balance deionized water. To the base solution, different strong acids were added and a corresponding amount of water (by weight) was omitted. The strong acids used are shown on the X-axis of the graph in FIG. 1. Each strong acid was added in two different scenarios: 1) at about 3.6% w/w, and 2) at about 0.0189 molar concentration.

The solutions with the strong acids and the NO ACID solution were subjected to corrosion tests as follows. Each solution was diluted with deionized water at a ratio of 1:40 and applied to bronze rod coupons with a length of 1 inch and a diameter of 0.5 inch. The corrosion tests were conducted in triplicate, with each trial involving fully submerging the bronze coupons in 100 ml of the diluted solutions in capped glass jars and incubating them in a 54° C. oven for a period of 3 hours. The severity of corrosion is demonstrated by the percent weight loss of each coupon by comparing the coupon's pre- and post-testing weights. The % weight loss was plotted in the graph shown in FIG. 1. The results demonstrate that non-surfactant organic sulfonic acids according to the invention, namely, p-toluene sulfonic acid, benzenesulfonic acid, methane sulfonic acid, 2-sulfosalicylic acid, and naphthalene disulfonic acid surprisingly cause less corrosion than the base NO ACID solution. This was unexpected since conventional wisdom holds that acids contribute to metal corrosion.

Accordingly, the present invention employs non-surfactant organic sulfonic acids which are "low-corrosive," meaning, that when the acids are used in the amounts disclosed herein, the acids would contribute to a maximum 20% increase in corrosiveness of the base formula, measured as a function of brass coupon weight loss, using the corrosion testing method and conditions disclosed herein. For example, the base NO ACID formula caused a 0.09% weight loss of the brass coupon in the present corrosion testing. Non-surfactant organic sulfonic acids which produce a corrosion level ≤0.09%×1.2, i.e. ≤0.108% are deemed low-corrosive.

Figure 2:
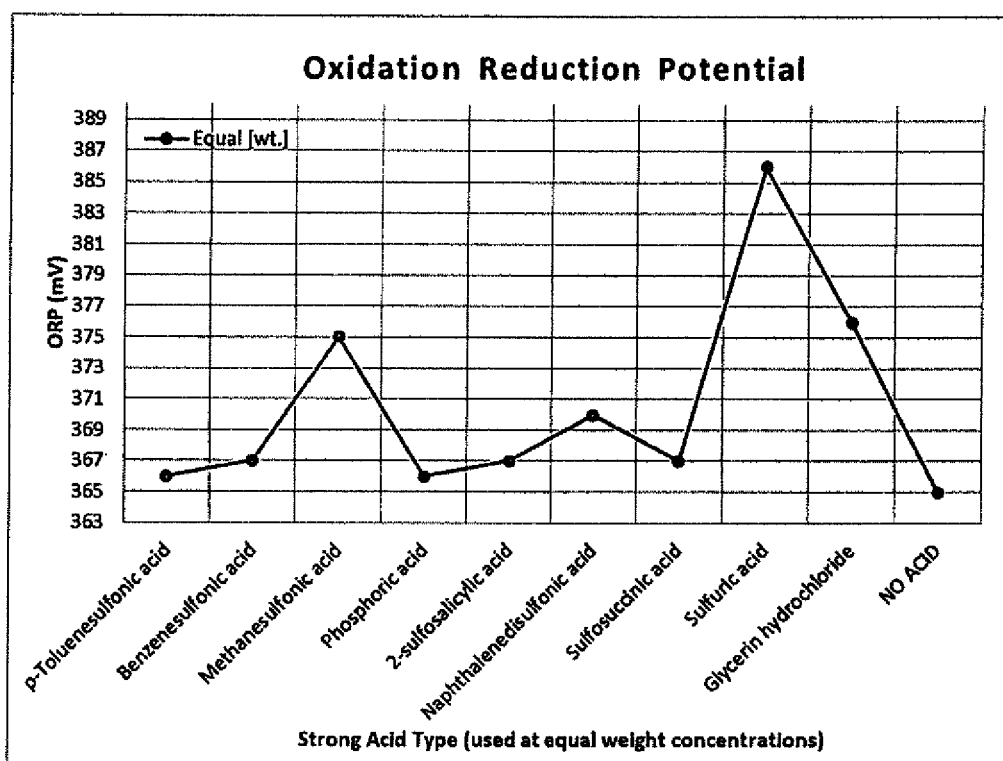
FIG. 2 is a graph depicting the standard reduction potential (SRP) of the solutions that underwent the corrosion testing.

The solution containing sulfosuccinic acid produced a higher level of corrosion than the NO ACID solution; however, this could be due to the nature of the metal substrate employed. As is shown in FIG. 2, sulfosuccinic acid has relatively low SRP value which suggests that the ingredient generally causes low corrosion. The solutions containing sulfuric acid, hydrochloric acid, and glycine hydrochloride are not in accordance with the invention.

Standard Reduction Potential (SRP)

The standard reduction potential of the solutions tested and for which the results are plotted in FIG. 1 are depicted in FIG. 2. The SRP of a solution generally references the metal corrosiveness of the solution. The SRP of each solution was measured using an Extech Instruments model SD100 pH/ORP meter at room temperature, and expressed in millivolts.

Comparing FIGS. 1 and 2, one can see that the SRP results shown in FIG. 2 correlate well to actual corrosion results shown in FIG. 1, except for sulfosuccinic acid and methane sulfonic acid. Sulfosuccinic acid has a relatively low SRP value (FIG. 2) but caused more corrosion than the NO ACID solution (FIG. 1). This may be due to the identity or nature of the bronze metal substrate. It is possible that the solution comprising sulfosuccinic acid would be less corrosive on other metal substrates. The SRP value for methane sulfonic acid is relatively high (FIG. 2) but the actual corrosion test results (FIG. 1) show that methane sulfonic acid is not highly corrosive in respect of the bronze metal substrate used in the tests. In sum, the non-surfactant sulfonic acids used in solutions according to the invention provide solutions that are, in general, low-corrosive.

The above description of embodiments is by way of example only and shall not be construed to limit the scope of the invention described and claimed. The person skilled in the art will appreciate that variations to the afore-mentioned embodiments are possible without departing from the scope of the invention.

The invention claimed is:

1. A shelf-stable, concentrated antimicrobial solution having a pH of from about 0 to about 3.5, the solution comprising:
   a. hydrogen peroxide at a concentration of from about 1.5% w/w to 8% w/w;
   b. at least one readily biodegradable anionic surfactant in a concentration of from about 10% w/w to about 25% w/w;
   c. at least one of salicylic acid and salts thereof, in a concentration of from about 1% w/w to about 8% w/w;
   d. at least one chelating agent in a concentration of from about 0.005% w/w to about 10% w/w;
   e. at least one low-corrosive non-surfactant sulfonic acid selected from the group consisting of benzenesulfonic acid, benzene disulfonic acid, xylene sulfonic acid, toluene sulfonic acid, cumene sulfonic acid, sulfosalicylic acid, naphthalene mono- or di-sulfonic acid, methane sulfonic acid, and isethionic acid in a concentration of from about 1% w/w to about 15% w/w;
   f. optionally, at least one nonionic surfactant in a concentration of from about 1% w/w to about 15% w/w;
   g. optionally, an effective amount of at least one additional ingredient selected from the group consisting of corrosion inhibitors, hydrotropes, dyes, defoamers, peroxide stabilizers, foam boosters, fragrances, pH adjusting agents, viscosity modifiers, soil suspenders, anti-redeposition agents, anti-freeze agents, solvents, additional strong acids, additional antimicrobial agents and diluents;
   h. at least one glycol ether solvent selected from the group consisting of tripropylene glycol methyl ether, tripropylene glycol n-butyl ether, polyethylene glycol phenyl ether, dipropylene glycol methyl ether, propylene glycol n-propyl ether, propylene glycol monomethyl ether, dipropylene glycol monopropyl ether, propylene glycol mono n-butyl ether, dipropylene glycol mono n-butyl ether, dipropylene glycol dimethyl ether, diethylene glycol mono-methyl ether, diethylene glycol monoethyl ether, ethylene glycol monopropyl ether, ethylene glycol monobutyl ether, diethylene glycol monobutyl ether, ethylene glycol monohexyl ether, diethylene glycol monohexyl ether, and ethylene glycol phenyl ether, in a concentration of from about 10% w/w to about 30% w/w; and
   i. water q.s. to 100;
   wherein the solution is substantially free of ingredients selected from the group consisting of peroxycarboxylic acids, acetic acid, furoic acid, phenylacetic acid, cationic surfactants, amphoteric surfactants, aromatic alcohols, halogen acids, phenols, peracid activators, and bleaches.

2. The solution of claim 1, wherein the pH is at least about 0.5.

3. The solution of claim 2, wherein the pH is at least about 1.

4. The solution of claim 1, wherein the at least one glycol ether solvent has a standard vapor pressure of less than 0.1 mm Hg.

5. The solution of claim 1, having a standard reduction potential (SRP) of from about 200 to about 400 mV.

6. The solution of claim 1, wherein the hydrogen peroxide is present in a concentration of from about 5 to about 8% w/w.

7. The solution of claim 1, wherein the at least one anionic surfactant is selected from alkyl aryl sulfonic acids.

8. The solution of claim 7, wherein the at least one anionic surfactant is a C8 to C18 alkyl benzenesulfonic acid.

9. The solution of claim 1, wherein the chelating agent is selected from the group consisting of etidronic acid (1-hydroxyethane 1,1-diphosphonic acid or HEDP), L-glutamic acid N,N-diacetic acid, methylglycine diacetic acid, and salts thereof.

10. The solution of claim 1, wherein the at least one non-surfactant sulfonic acid is chosen from benzenesulfonic acid, naphthalene disulfonic acid, and toluene sulfonic acid.

11. The solution of claim 1 diluted with water in a ratio of from 1:10 to 1:300 (solution:diluent).

12. The solution of claim 11 diluted with water in a ratio of from 1:16 to 1:256 (solution:diluent).

13. The solution of claim 1, wherein a pH adjuster is present in an amount to adjust the pH of the solution to said pH range.

14. The solution of claim 1, wherein at least one nonionic surfactant is present and chosen from the group consisting of alcohol ethoxylates and block copolymers.

15. The solution of claim 1, wherein the solution is free of volatile organic compounds (VOCs).

16. The solution of claim 1, wherein the at least one chelating agent is chosen from the group consisting of tertiary amine-based chelating agents, phosphonate-based chelating agents, and salts thereof.

17. The solution of claim 1, wherein the at least one readily biodegradable anionic surfactant is chosen from the group comprising alkyl sulfonic acids, alkyl aryl sulfonic acids, alkyl sulfuric acids, sulfonated carboxylic acids, alkyl sulfonic acids, and alkyl or alkenyl esters or diesters of sulfosuccinic acids, and alkali metal, ammonium, calcium and magnesium salts thereof.

18. The solution of claim 17, wherein the at least one readily biodegradable anionic surfactant is chosen from the group comprising alkyl sulfonic acids, alkyl aryl sulfonic acids, alkyl sulfates, and salts thereof.

19. The solution of claim 1, wherein the solution is also free of benzoic acid.

20. A method for disinfecting a hard or soft surface, the method comprising applying to said hard or soft surface a solution according to claim 1, wherein the solution provides at least a two-log reduction of a bacteria at a maximum contact time of 5 minutes at room temperature and at a maximum 1:64 (solution:diluent) dilution using test method ASTM E1153.

21. The method of claim 20, wherein the solution also provides at least a one-log reduction of mycobacteria at a maximum contact time of 5 minutes at room temperature and at a maximum 1:40 (solution:diluent) dilution using test method AOAC 965.12.

22. A ready-to-use antimicrobial solution produced by combining a solution according to claim 1 with a diluent at a ratio of from 1:2 to 1:256 (solution:diluent).

23. A dry composition which, when combined with a liquid diluent produces a solution according to claim 1.

24. A dry composition which, when combined with a liquid diluent, produces a solution according to claim 22.

* * * * *

UNITED STATES PATENT AND TRADEMARK OFFICE
CERTIFICATE OF CORRECTION

PATENT NO. : 10,450,535 B2
APPLICATION NO. : 15/786632
DATED : October 22, 2019
INVENTOR(S) : Faraz Ahmadpour and Navid Omidbakhsh Page 1 of 1

It is certified that error appears in the above-identified patent and that said Letters Patent is hereby corrected as shown below:

On the Title Page

Under item (72) Inventor delete:
"Faraz Ahmadpour, Mississauga (CA)"

And replace with:
--Faraz Ahmadpour, Mississauga (CA)
Navid Omidbakhsh, Mission Viejo, CA (US)--

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*